United States Patent [19]  [11] Patent Number: 4,848,904
Sapp et al.  [45] Date of Patent: Jul. 18, 1989

[54] DUAL BEAM MULTICHANNEL SPECTROPHOTOMETER WITH A UNIQUE LOGARITHMIC DATA CONVERTER

[75] Inventors: Edwin R. Sapp, Hillsdale; Eric K. Kinast, Westwood, both of N.J.

[73] Assignee: Applied Biosystems Inc., Foster City, Calif.

[21] Appl. No.: 156,285

[22] Filed: Feb. 16, 1988

[51] Int. Cl.⁴ .............................................. G01J 3/42
[52] U.S. Cl. ................................... 356/319; 250/565
[58] Field of Search ............... 356/306, 319, 320, 323, 356/325, 326, 328, 408, 432, 433, 434, 435; 250/565

[56] References Cited

U.S. PATENT DOCUMENTS

| Re. 28,803 | 5/1976 | Durkos | 356/306 |
| 3,952,206 | 4/1976 | Liedholz | 250/565 |
| 4,124,301 | 11/1978 | Pocock | 356/432 |
| 4,678,917 | 7/1987 | Helms et al. | 356/328 |

Primary Examiner—F. L. Evans
Attorney, Agent, or Firm—Morgan & Finnegan

[57] ABSTRACT

The present invention relates to an improved dual beam multichannel spectrophotomer employing a simple and novel optical system in combination with photodiode arrays and a unique logrithmic data converter to convert light signals to absorbance. In particular, the optical system utilizes optical elements in a novel arrangement to direct a pair of equivalent sample and reference beams in an essentially parallel formation respectively through a sample and reference cell and to focus and direct the emergent sample and reference beams to a single flat horizontally ruled grating which disperses each of the sample and reference beams respectively onto a pair of vertically disposed photodiode arrays whereby the light signals are converted into absorbance units (AU) by an unique logarithmic data converter. The spectrophotometer is highly accurate, has very low drift, less than $2\times10^{-4}$ AU/°C., and very low noise, less than $\pm 2\times10^{-5}$ AU. The dual beam multichannel spectrophotomer is particularly suitable for use in high pressure liquid chromatography to record the absorbance spectrum of the samples as they are being eluted from the chromatographic column.

14 Claims, 6 Drawing Sheets

DUAL BEAM MULTICHANNEL SPECTROPHOTOMETER WITH A UNIQUE LOGARITHMIC DATA CONVERTER

The present invention relates to an improved dual beam multichannel spectrophotometer employing a simple and novel optical system in combination with photodiode arrays and a unique logrithmic data converter to convert light signals to absorbance. In particular, the optical system utilizes optical elements in a novel arrangement to respectively direct a pair of equivalent sample and reference beams in an essentially parallel formation through a sample and reference cell and to focus and direct the emergent sample and reference beams to a single flat horizontally ruled grating which disperses each of the sample and reference beams respectively onto a pair of vertically disposed photodiode arrays whereby the light signals are converted into absorbance units (AU) by an unique logarithmic data converter. The spectrophotometer is highly accurate, has very low drift, less than $2\times 10^{-4} AU/°C.$, and very low noise less than $\pm 2\times 10^{-5} AU$.

The dual beam multichannel spectrophotometer is particularly suitable for use in high pressure liquid chromatography to record the absorbance spectrum of the samples as they are being eluted from the chromatographic column.

BACKGROUND OF THE INVENTION

In liquid chromatography, samples are separated by a chromatographic column. The components separated from the sample are traditionally detected by means of a refractometer or a spectrophotometer. Since the refractometer does not distinguish one chemical from another, a spectrophotometer, in particular a UV spectrophotometer, is preferred. Double beam U.V. spectrophotometers have been employed in liquid chromatography, particularly high pressure liquid chromatography (HPLC) for many years.

One such double beam U.V. spectrophotometer for HPLC was described in Schoeffel et al, U.S. Pat. No. 3,985,441. The optical system employed a pair of multi-directional refocusing optical mirrors to direct two identical areas of light from a single light source onto a single grating which disperses the beams into a pair of spectra. A pair of apertures permit only light with a very narrow selected range of wavelengths from the pair of spectra to be passed through a pair of optical cells. The emergent light beams impinge on a pair of photodetectors, the signals of which are converted to absorbance units by an analog logarithmic ratio circuit.

However, conventional UV spectrophotometers used for HPLC can only record absorbance at a single narrow band of wavelengths. Thus, not all of the sample components can be detected at their optimum absorbance. In fact, some components may not be detected at all, if these components did not absorb UV light at the selected wavelengths.

Attempts have been made to develop multiwavelength spectrophotometers for HPLC. The first generation of such instruments employed moving mechanical parts to scan the spectrum, typified by using rotating mirrors or vibrating galvanometers. The second generation utilized Vidicon tubes. However, these systems are very expensive and tend to show memory and blooming which makes them suitable as interim solutions only. See Dessy et al., *J. of Chroma. Sci.*, 14, pp. 195–201 (April 1976).

Dessy et al. describes one system which employed photodiode arrays to provide a means for recording the spectrum of each component separated in HPLC. The light from the source, a deuterium lamp or a xenon lamp, is directed by a light pipe of optical fibers onto the sample and reference cells of a HPLC unit. The light is then redirected by means of light pipes to a pair of concave holographic gratings to focus and disperse the light beams onto a pair of photodiode arrays. The signals from the photodiode array are processed through an analog-log converter circuit into readable form. The total amount of time required to record a spectrum is about 3.1 seconds. This is much too slow to make recordings of the spectra of components as these are being eluted from the chromatographic system. Moreover, the geometry of the optical systems is such that the photodiode array must be offset away from the flow cells to avoid interference from the undispersed light beam. This means that the housing for the optical systems is rather bulky.

Another early dual beam spectrophotometer was commercialized by Hitachi. The Hitachi 635M dual beam channel UV detector utilized deuterium lamp as the source. The beams were split, directed through a pair of flow cells on to an astigmatic concave replica grating which dispersed and at the same time focused the beams onto photocell arrays with eight channels. The signals from the eight pairs of photocell array with one pair for each selected wavelength were monitored. This represented an improvement over single wavelength recording. However, it can not be utilized for full spectrum recording. Moreover, it has a similar optical arrangement to Dessy et al. and has similar disadvantages.

U.S. Pat. No. 4,678,917 issued July 7, 1987, describes a method and apparatus for taking instantaneous readings from a multichannel spectrophotometer. The beam from a light source is split and both beams were respectively directed to reflectors and passed through a sample cell and a reference cell. The radiation from each of the cells was directed to a diffraction grating which disperse the beam into a polychromatic divergent beam and direct the beam on a linear array of photodetectors. The signals from the photodetectors were carried through separate signal channels into sample-and-hold circuits controlled by a multiplex switch which operates in response to control signals from a sequence control. The multiplex switch causes the sample-and-hold circuits to sample and hold the signals which are read out of the analog mode and converted to digital mode. The digitized data is stored and processed by a data processing unit which may be a digital computer and presented as absorbance units versus wavelength. This instrument is capable of full spectrum recording.

The spectrophotometer described in U.S. Pat. No. 4,678,917 has several disadvantages. The analog-to-digital converter utilized in U.S. Pat. No. 4,678,917 calls for complex circuitry which is rather costly. The optical system as depicted produces a pair of unfocused divergent beams on the photodiode arrays and will cause problems in increased noise level. Moreover, the heat from the light source being close to the sample cells, would affect the cells and cause additional errors in the results obtained. Thus to avoid all of these problems, a different optical arrangement is required. It is the object of the present invention to develop a dual beam spectrophotometer that is accurate, compact and stable, but less costly.

It is another objective of the present invention to develop a dual beam spectrophotometer with a simple and less costly optical system wherein the light source, the reference and sample cells and the photodetectors are isolated from one another resulting in a system which is a stable and has very low drift.

It is a further objective of the present invention to develop a signal converter for the simultaneous recording of the signals from a multichannel full spectrum spectrophotometer that utilizes a simple circuitry and is less costly.

SUMMARY OF THE INVENTION

The present invention relates to a full spectrum multichannel spectrophotometer comprising:

A. a single light source;

B. an aperture defining a cone of light from the light source;

C. a first pair of concave front surface mirrors reflecting and directing a pair of equivalent light beams, a reference beam and a sample beam, from the cone of light respectively on to a pair of flat front surface mirrors which respectively redirect the reference beam and the sample beam to a pair of optical cells, a reference cell and a sample cell, the first pair of concave front surfaced mirrors and the flat front surfaced mirrors being arranged such that the first pair of concave front surfaced mirrors focus the beams on the optical cells respectively and that the angle between the incident light beam and the reflected light beam is less than 20°;

D. a second pair of concave front surface mirrors for directing the beams from the reference cell and sample respectively to a single flat grating for dispersing each of the beams into a spectrum, and redirecting the reference beam and the sample beam to a reference photodiode array and a sample photodiode array, the second pair of concave front surface mirrors and grating being arranged such that the second pair of concave front surface mirrors focus the beams on the respective photodiode arrays and that the angle between the incident light beam and the reflected light beam at the concave mirrors and the grating is less that 20°;

E. the reference photodiode array and the sample photodiode with from about 30–70 elements intercept each of the spectra and convert the light intensity of each beam respectively to a reference electrical signal and a sample electrical signal; and F. a data converter to convert the electrical signals from the pair of photodiode arrays into light absorbance units.

The full spectrum multichannel spectrophotometer further comprises a logarithmic data converter comprising:

(i) a means for selecting the electrical signals corresponding to a particular reference photodiode and sample photodiode;

(ii) a means for converting each of the electrical signals to a voltage signal;

(iii) a means for storing the reference signal and discharging the reference signal voltage to exponentially decay to the sample signal voltage level;

(iv) a means for determining the time interval in which the reference signal voltage decays to the sample signal voltage, wherein the time interval is proportional to the logarithm of the ratio of the reference signal voltage to the sample signal voltage and wherein such logarithm is proportional to the absorbance of light by the sample; and (v) means for repeating steps (i) through (iv) for each pair of the reference electrical signal and sample electrical signal in each element of the photodiode arrays.

DETAILED DESCRIPTION OF THE INVENTION

Figure 1:
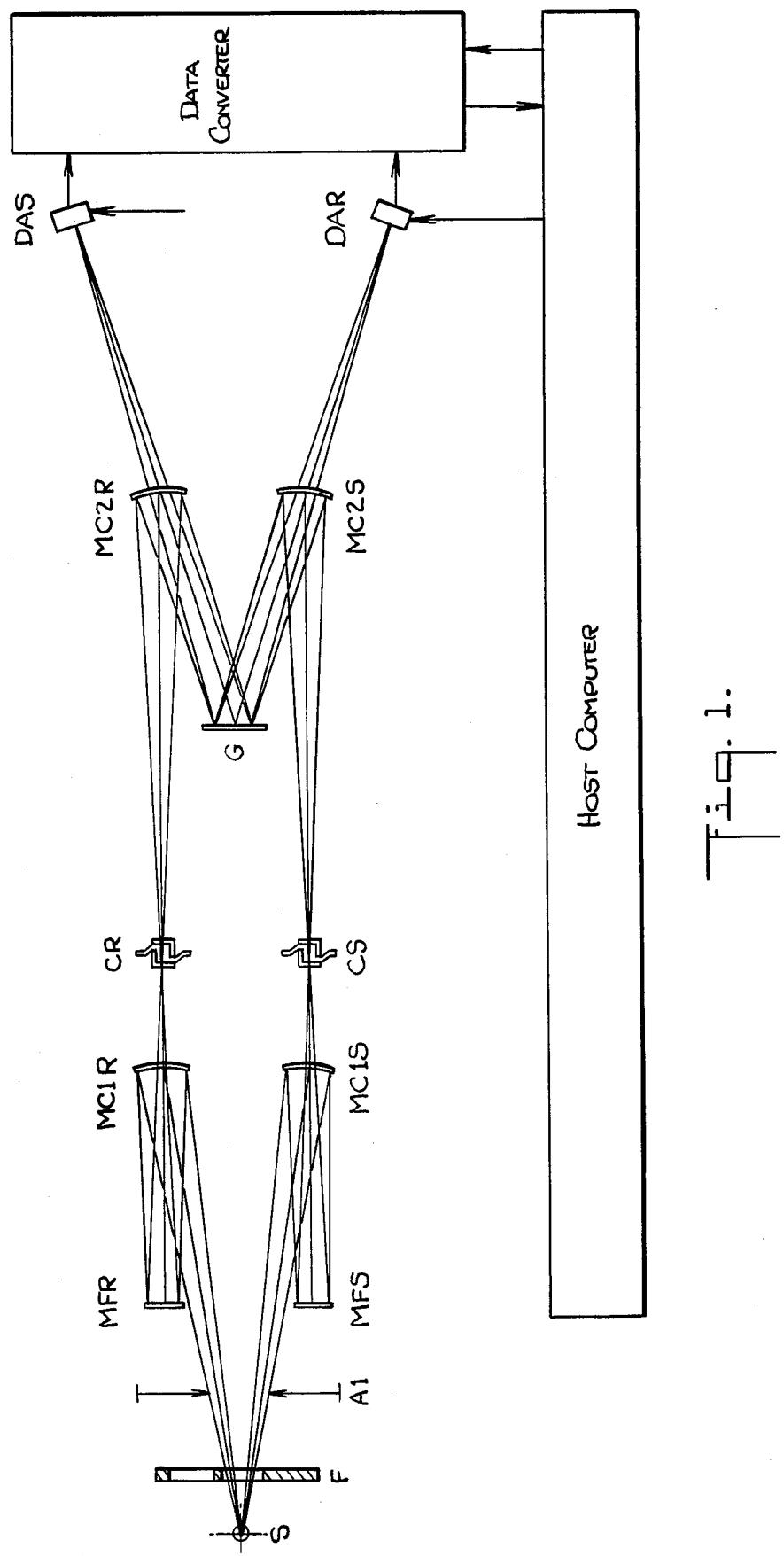
FIG. 1 is a schematic diagram of the spectrophotometer of the present invention.
Figure 2:
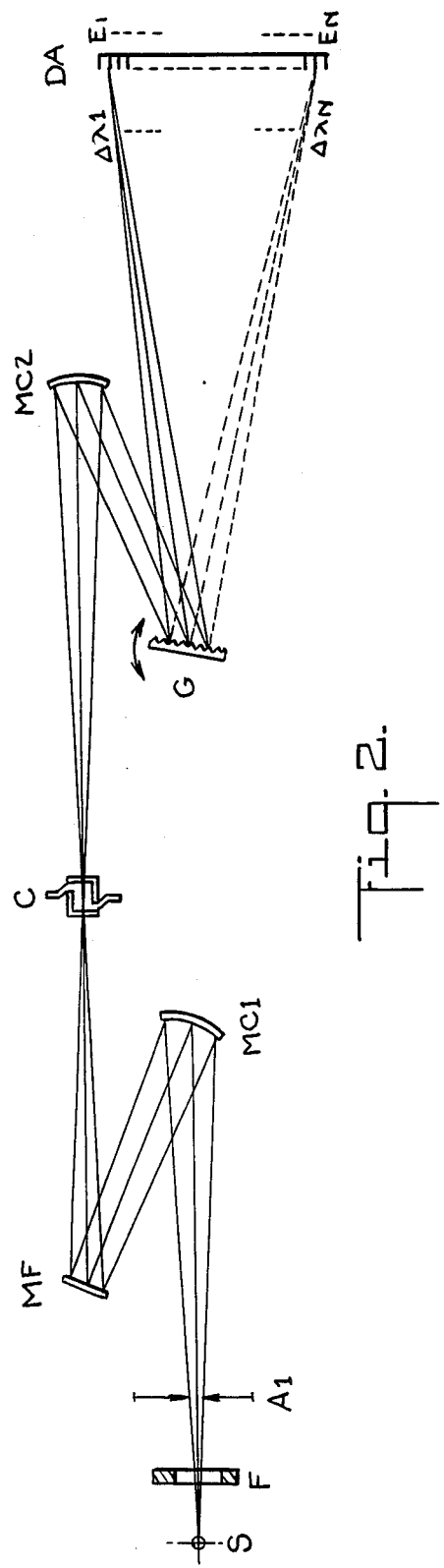
FIG. 2 is a side view of the optical system wherein the horizontally ruled flat grating is rotated to a second position to permit a different region of the spectrum to be focused on the photodiode array.

The present invention is directed to a full spectrum multichannel spectrophotometer comprising:

A. a single light source;

B. an aperture defining a cone of light from the light source;

C. a first pair of concave front surface mirrors reflecting and directing a pair of equivalent light beams, a reference beam and a sample beam from the cone of light source respectively on to a pair of flat front surface mirrors which respectively redirects the reference beam and the sample beam to a pair of optical cells, a reference cell and a sample cell, the first pair of concave front surfaced mirrors and the flat front surfaced mirrors being arranged such that the first pair of concave front surface mirrors focus the beams on the optical cells respectively and that the angles between the incident light beam and the reflected light beam at the first pair of concave front surface mirrors and the pair of flat front surface mirrors are less than 20°;

D. a second pair of concave front surface mirrors for directing the beams from the reference cell and sample cell respectively to a single flat grating for dispersing each of the beams into a spectrum, and redirecting the reference beam and the sample beam to a reference photodiode array and a sample photodiode array, the second pair of concave front surface mirrors and grating being arranged such that the second pair of concave front surface mirrors focus the beams on the respective photodiode arrays and that the angle between the incident light beam and the reflected light beam at the second pair of concave front surface mirrors and the grating are less that 20°;

E. the reference photodiode array and the sample photodiode with from about 30–70 elements intercept each of the spectra and convert the light intensity of each beam respectively to a reference electrical signal and a sample electrical signal; and F. a data converter to convert the electrical signals from the pair of photodiode arrays into light absorbance units.

In a preferred embodiment the angles between the incident light beam and the reflected light beam at the first pair of concave front surface mirrors are approximately 12.4 degrees and at the pair of flat front surface mirrors are about 11.5 degrees, whereas the angles between the incident light beam and the reflected light beam at the second pair of concave front surface mirrors and at the grating are both about 15.8 degrees.

The dual beam multichannel spectrophotometer of the present invention is suitable for the recording of the absorbance spectrum of light absorbing compounds from about 190 nm to 700 nm. It is particularly suitable as a detector for a HPLC apparatus wherein the sample cell is in the form of a flow cell connected to the end of the separation column from which sample is being eluted.

The dual beam multichannel spectrophotometer of the present invention eliminates many problems associated with variations of source energy output over time, grating efficiency, mirror coating and photodetector response as a function of wavelength. Moreover, the dual beam multichannel spectrophotometer of the present invention is compact and less expensive; employing simple, inexpensive optical elements in an optical arrangement wherein the reference and sample light beams are essentially parallel, the reference and sample flow cells are away from the light source and the photodiode arrays are isolated from the light source and the sample and reference cells.

The optical system employs simple, inexpensive optical components which permits the directing of light beams from a single light source through a simplified optical path. The hot light source is located away from the sample and reference cells to avoid any temperature effects. The light dispersion section is designed in such a manner that only three components, two concave front surface focusing mirrors and a flat grating is used. The grating can be rotated from a first position for a shorter wavelenqth region to a second position for the longer wavelength region of the spectra onto the reference and sample photodiode arrays.

The multichannel spectrophotometer of the present invention may further comprise a unique logarithmic data converter circuit which uses simple circuitry to automatically convert the signals from the sample and reference photodiode arrays into absorbance units. Using this method of data conversion any variation due to source energy fluctuation is automatically eliminated. Moreover, because of the simplicity of the circuitry, cost is greatly reduced.

The instrument is shown in FIG. 1, including the optics and data converter, along with the host computer (in block diagram format). The source of optical radiation S, is typically a deuterium or xenon lamp for the UV region. A tungsten-halogen lamp can be used if absorbance in the visible region is desired. A cone of light shaped by an aperture, A1, is reflected by front surface concave mirrors MC1R and MC1S, to form a reference beam and a sample beam and focus each beam respectively via a pair of flat front surface mirrors, MFR and MFS, which redirect the beams respectively onto a sample cell and a reference cell, both equipped with optical windows. For HPLC applications, the cells are low volume flow cells. Alternatively, the reference cell may be replaced by a precision aperture.

After passing through the cells, or flow cells, each beam is intercepted by front surfaced concave mirrors, MC2R and MC2S, and directed onto a single horizontally ruled grating which respectively reflects and disperses the beams onto a pair of matched photodiode arrays. The concave front surfaced mirrors also focus the dispersed beams onto the respective photodiode arrays. Each diode element, $E_i$, in the photodiode array collects the light from the dispersed beam over a given wavelength band, $dL_i$. The range of wavelengths collected by the photodiode array for a given angular position of the grating is the sum of the wavelength bands for each element in the array.

The concave front surfaced mirrors, flat front surfaced mirrors and grating are arranged so that for each light beam, the angles between the incident beam and the reflected beam are less than 20°. In this manner, the reference and sample beams are maintained in a substantially parallel formation and the light source, the sample and reference cells and photodiode arrays can be isolated from one another in an essentially straight tunnel-like formation. In a preferred embodiment, the angles between the incident beam and the reflected beams at the first pair of concave front surfaced mirrors are about 12.4° and at the flat front surface mirrors are about 11.5°, and the angles between the incident beam and reflected beams at the second pair of concave front surface mirrors and the grating are both about 15.8°.

Each wavelength element in the sample array, $E_iS$, has a corresponding wavelength element in the reference array, $E_iR$. The log of the ratio of the voltage generated is proportional to the absorbance of the chemical compounds in the sample cell for the given wavelength band. The absorbance is proportional to the concentration of the compounds in the sample cell and thus can be used to quantitate the amount of the chemical compound of interest. By comparing successive elements in the two arrays, the absorbance as a function of the wavelength can be generated.

By changing the tilt of the grating, a different wavelength range can be selected. A movable filter holder, F, may interpose a filter into the beam between the source and the first pair of concave front surfaced mirrors to eliminate possible second order effects in the longer wavelength regions (See FIG. 1). Another portion of the filter holder can be positioned to block the beams for checking the dark current of the arrays.

A unique logarithmic data converter is designed for use with the photodiode arrays. The non-linear data converter is a type of ratiometric and logarithmic data converter with simple circuitry that is economical to manufacture.

Figure 4:
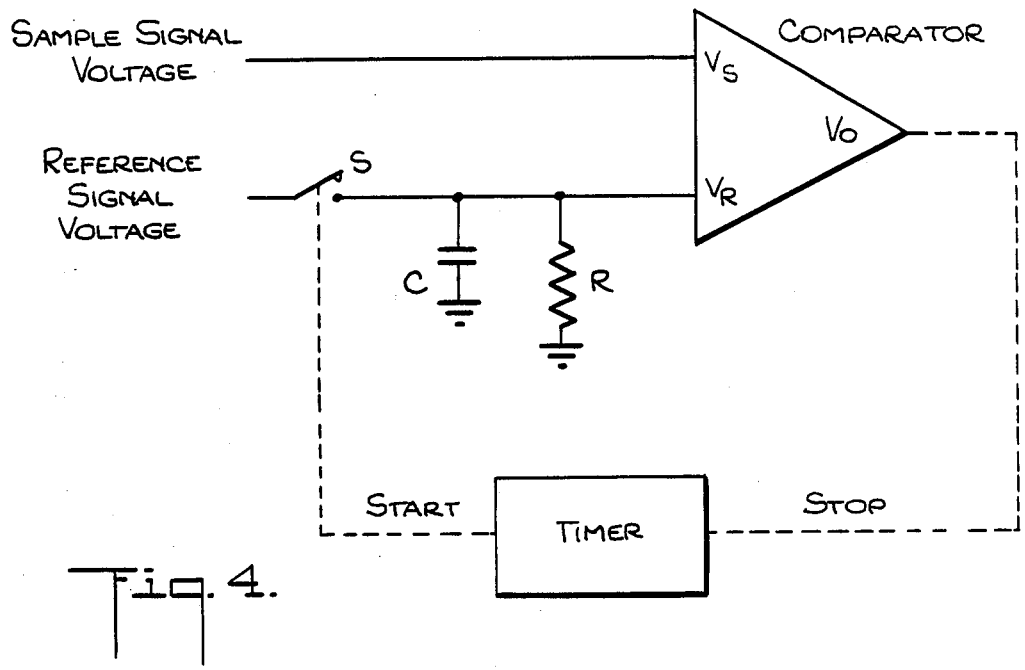
FIG. 4 is a schematic of data converter circuitry illustrating the beam intensity to sample absorbance conversion concept.
Figure 5:
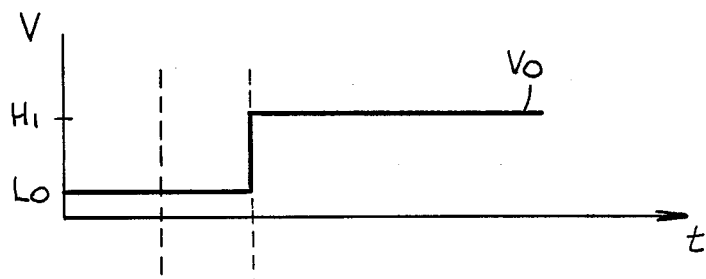
FIG. 5 illustrates the timing diagram for the converter circuit of FIG. 4.

FIG. 4 is a simplified version of the log converter circuit for purposes of illustrating the beam intensity to sample absorbance conversion concept. FIG. 5 shows the timing diagram for the converter circuit of FIG. 4. A sample signal voltage, $V_s$, and a reference signal voltage, $V_r(O)$, each corresponding to respective beam intensities at an identical beam wavelength, are input to the data converter circuitry.

An ideal switch, S, is initially closed, bringing the capacitor voltage to the desired initial voltage level, $V_r(O)$. Then simultaneously, the switch is opened and the timer is started. When the comparator senses that the capacitor C voltage has decayed to the sample voltage, the timer is stopped. The time interval, which is proportional to sample absorbance is the output of the converter. The conversion process then is repeated for additional pairs of sample electrical signal and reference electrical signal inputs from the photodiode array to generate a spectrum of sample absorbance over many wavelengths. Once the photodiodes arrays have been sampled to produce a multiwavelength spectrum, the cycle may be repeated to provide a series of multiwavelength spectra over time.

Referring to the timing chart of FIG. 5, which shows the comparator input and output signals for one data conversion, switch S, initially, is closed and Capacitor C, charged to the reference signal voltage level. As a result, the comparator input $V_r$ equals the reference signal voltage, while the comparator input $V_s$ equals the sample signal voltage. Because the reference signal voltage is greater than the sample signal voltage, the comparator output, $V_0$, is in the state for $V_r$, greater than $V_s$.

At time, $t_0$, switch S is opened and Capacitor C discharges through resistor R. When the Capacitor C discharges to the sample signal voltage level, the comparator output, $V_0$, flips triggering the timer to stop. This time is designated $t_1$. The time interval between $t_0$ and $t_1$ is T. The comparator input $V_r(t)$ is given by the formula:

$$V_r(t) = V_r(0) e^{-t/rc} \tag{1}$$

Transposing formula (1) yields:

$$\ln [V_r(0)/V_r(t)] = (1/RC)t \tag{2}$$

$$\text{or } \log [V_r(0)/V_r(t)] = (\ln 10/RC)t \tag{3}$$

At the end of time interval T, $V_r(T) = V_s$:

$$\log [V_r(0)/V_s] = (\ln 10/RC)T = kT \tag{4}$$

where $k = \text{constant} = \ln 10/RC$.

Knowing that the absorbance is directly proportional to the logarithm of the ratio of the reference signal voltage to the sample signal voltage, $\log [V_r(0)/V_s]$, the time interval, T, provides an indication of absorbance.

Figure 6:
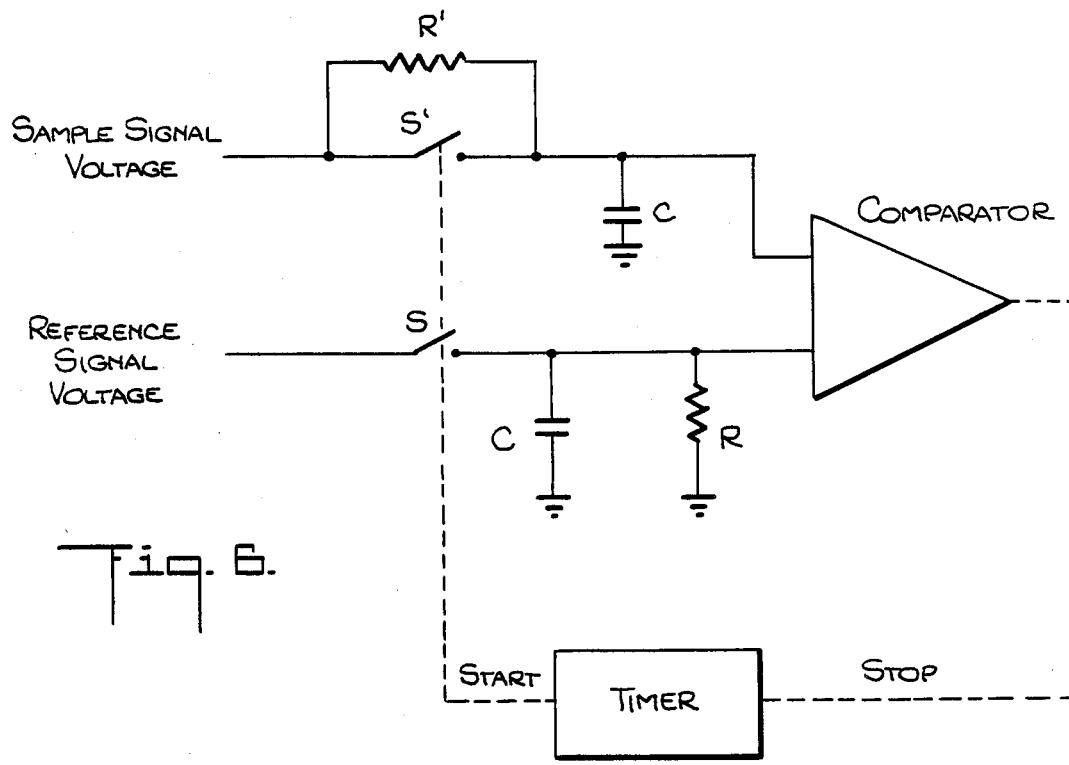
FIG. 6 represents a practical embodiment of the logarithmic converter circuit to account for charge injection by switch S, and input bias currents to the comparator.
Figure 7:
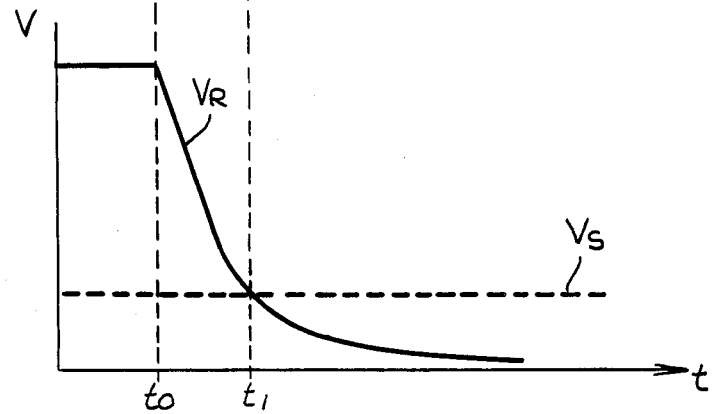
FIG. 7 is the timing diagram for the circuit of FIG. 6.

FIG. 6 represents a practical embodiment of the log converter circuit to account for charge injection by switch S, and input bias currents to the comparator. FIG. 7 is a timing diagram for the circuit of FIG. 6. Because solid state switches tend to inject a small amount of charge when switched, a small shift in the initial capacitor voltage occurs at the time the switch is opened. To account for the small shift an additional switch S' is added in the sample signal voltage path. As a result, the same shift will occur in both the reference signal voltage path and the sample signal voltage path. Preferably, S' and S are two elements of the same monolithic integrated circuit. However, it is only necessary that the switches S and S' have substantially identical parameters.

To account for input bias currents which may cause an undesired error voltage to be generated on the RC network, identical impedances are provided at both input channels to the comparator. Thus, a resistor, R', and capacitor, C', are added to the sample signal voltage path. Preferably R' and C' are of the same type and values as their counterparts R and C. The connection for R' and C', however, varies from the connection of R and C so that capacitor C' will not discharge.

The modifications added to the circuit of FIG. 6 cause the switch charge injection and comparator bias currents to be substantially equal at both input channels to the comparator. Thus the injection and bias currents are presented as common-mode signals substantially eliminating any impact on the comparator output.

With regard to the operation of the log converter embodiment of FIG. 6, switches S and S' initially are closed causing capacitor C to be charged to the reference signal voltage level and capacitor C' to be charged to the sample signal voltage level. At time $t_0$, the switches are opened and the timer begins to count. As with the circuit of FIG. 4, the opening of switch S causes capacitor C to discharge through resistor R. When capacitor C discharges to the sample signal voltage level the comparator output flips triggering the timer to stop. This time is designated $t_1$ and the time interval between $t_0$ and $t_1$ is designated T. As with the circuit of FIG. 4, the formula describing $V_r(T)$ is:

$$\log [V_r(0)/V_s] = (\ln 10/RC)T = kT$$

where $k = \text{constant} = \ln 10/RC$.

The absorbance similarly is directly proportional to the time interval, T.

Figure 3:
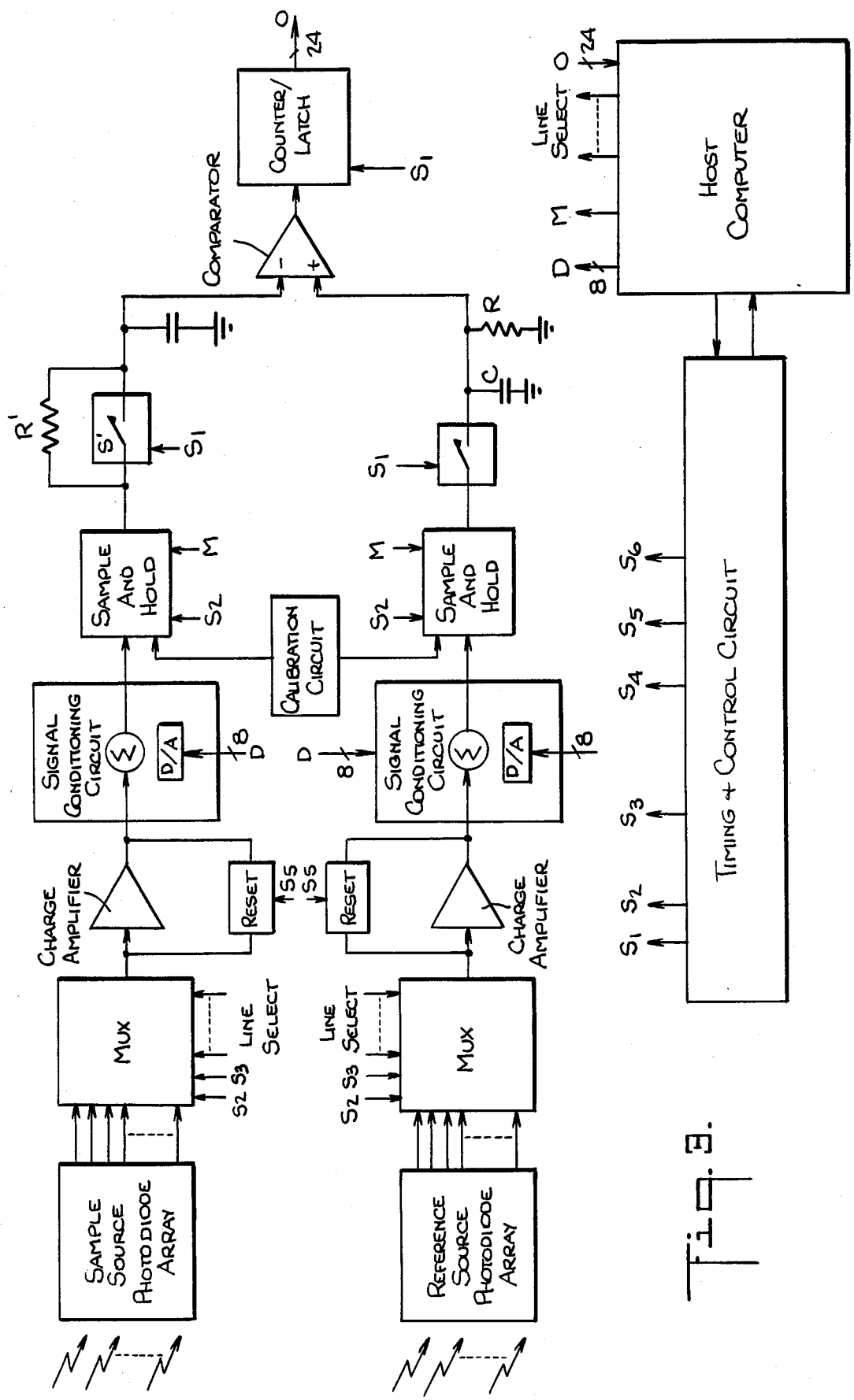
FIG. 3 is a schematic of the electronics of the spectrophotometer used in the present invention.
Figure 8:
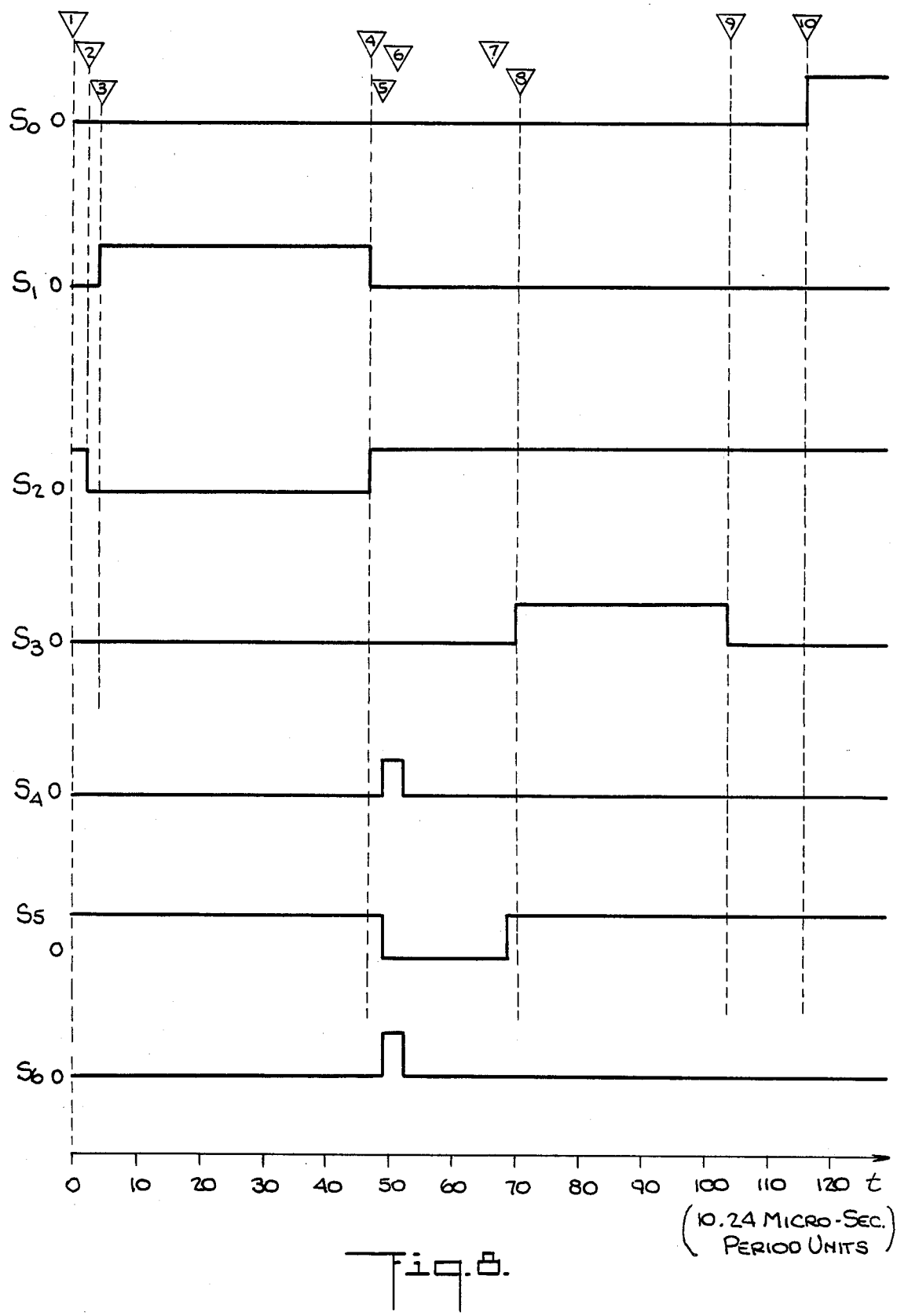
FIG. 8 is a timing diagram for timing signals $S_0$–$S_6$ of the circuit of FIG. 3.

FIG. 3 illustrates the photodiode array circuits and the log converter circuit embodied to provide for multiwavelength absorbance detection. FIG. 8 is a timing diagram for timing signals $S_0-S_6$.

After each of the dual beams impinge upon the flat grating, each beam is diffracted into a multiwavelength spectral beam. The multiwavelength spectral beam associated with the sample source strikes the sample source photodiode array, while the spectral beam associated with the reference source strikes the reference source photodiode array. Each photodiode array may include about 30–70 diodes, preferably 40, most preferably 38 diodes. The light striking each diode is at a specific wavelength different from the wavelength of the light striking other diodes. Both the sample signal channel and reference signal channel include a multiplexer for selecting which photodiodes are to be read. The multiplexer select lines for each channel correspond so that the photodiode selected for the sample channel and the photodiode for the reference channel are corresponding photodiodes which receive light at the same wavelength from the respective beams. The photodiodes in each array are read sequentially, such that the signal outputs from the photodiode arrays are pipelined through the data converter circuit in serial sequence. The sample signal goes through the sample source channel, while the corresponding reference signal goes through the reference channel. As illustrated, the host computer provides the line select for determining the sequence of sampling the photodiode arrays. However the line selects may be determined from another source or automatically programmed to sequentially access the diodes within the arrays.

The respective sample and reference signals go through respective charge amplifiers to convert the signals to a signal voltage. The voltage signals then pass through respective charge conditioning circuits.

The charge conditioning circuits each include a resistor network for summing to the sample voltage or reference voltage, correction voltages to compensate for photodiode dark current errors and multiplexer charge injection. The correction voltages are inputted from the host computer to the respective resistor networks via a digital to analog converter. The sample signal voltage and reference signal voltage then enter respective sample and hold circuits. In one embodiment, each of the sample and hold circuits includes a multiplexer for selecting either the on-line sample signal voltage and reference signal voltage or alternative calibration signals which enable calculation of the correction voltages. The input, M, originating at the host computer determines the mode in which the sample and hold circuits operate.

After being output from the sample and hold circuits, the sample signal voltage and reference signal voltage then enter the data converter circuit. The data converter circuit corresponds to the circuit as described for FIG. 6, although the counter/latch corresponds to the timer of FIG. 6. The count that is latched into the counter is proportional to the sample absorption and is read and processed by the host computer to be formatted, stored and/or displayed.

The pipelining of sample and reference signals, including the charge to voltage conversion, signal conditioning and logarithmic conversions are controlled by the timing and control circuit of FIG. 3. The timing and control circuit may be a PLA, ROM look-up table, discrete logic circuitry, CPU or other circuitry capable of cyclically generating timing signals for the data conversion process. In the preferred embodiment the timing signals include signals $S_0$ through $S_6$ as illustrated in the timing diagram of FIG. 8. The timing of the FIG. 3 circuit is illustrated in FIG. 8 by the timing signals $S_0$ to $S_6$.

Referring to FIG. 8, at point 1, the system has been idle awaiting to be triggered by the host computer. The system remains inactive for 1 clock pulse after the trigger.

At point 2, the sample and hold circuit is strobed, via $S_2$, to acquire data from the signal conditioning circuit. This signal is the charge amplifier output from the discharged photodiode, modified by the dark current correction supplied by the host computer during the previous cycle.

At point 3, data from the previous conversion is clocked from counters to data registers on the rising edge of $S_1$. This signal also clears the counter and initializes the data converter capacitors, C' and C, for the next conversion.

At point 4, the falling edge of $S_1$ starts the data converter action by opening the analog switches, S and S', enabling the counters. The sample and hold circuits are put to a "hold" condition via $S_2$, to provide a sustained signal to data conversion.

At Point 5, $S_5$ is brought low to reset the charge amplifier so as to prepare for the next pair of signals from the sample beam photodiode array and reference beam photodiode array.

At point 6, signal $S_6$ initiates a host computer request for interrupt service, while signal $S_4$ strobes the multiplexer to load the line select and prepare for transferring the next sample signal and reference signal from the respective photodiode arrays.

Sometime between point 6 and the start of the next cycle (at Point 1), the host computer will service the interrupt and (1) read the data from the counter/latch, (2) output the number of the next photodiodes to be selected to the multiplexers, and (3) output the dark current corrections for the next signals to enter the signal conditioning circuit. Because of the pipeline sequencing of photodiode array outputs, the host computer deals with different operations on the sample signals and reference signals at once. For example, if sample signal voltage (N) is currently being converted by the data converter section, then the absorbance output (N−1) is being read from the counter/latch, while dark current corrections are being provided to the signal conditioning circuit for sample signal voltage and reference signal voltage (N+1), and the sample signal and reference signal (N+1) are the signals about to be introduced to the charge amplifier. Additionally, the host computer is generating the line select signals for diode numbers for signals (N+2).

At point 7, the reset signal is removed from the charge amplifier, and the system is allowed to remain idle for a settling time.

At point 8, the photodiode multiplexers are enabled to transfer a sample signal and reference signal from the respective photodiodes to respective charge amplifiers.

At point 9, the multiplexer is disabled, opening the input circuit of the charge amplifier. The charge amplifier output will thus remain stable awaiting acceptance (after conditioning) by the sample and hold circuits on the next cycle.

At point 10, $S_0$ goes high, inhibiting data flow until the timing generator triggers the next cycle restarting the timing sequence from point 1.

The time scale on the timing diagram of FIG. 8 is in clock periods of 10.24 microseconds. The complete flow sequence for a one wavelength conversion therefore takes approximately 1.223 milliseconds. The interval between cycles is normally 2.50 milliseconds, although the timing generator is inhibited for approximately ½ this time. For approximately 40 diodes per photodiode array, the conversion for an entire spectrum takes approximately 0.1 second. Because the sample signal and reference signal outputs are pipelined through in real time and are not simply a frozen snapshot of the approximately 40 pairs of photodiode charges, there is a slight variation in time between the conversion for the signal at the first wavelength and the conversion for the signal at the last wavelength of the spectrum. The absorbance outputs from the counter/latch may be formatted by the host computer to generate a three dimensional plot of sample absorbance vs. beam wavelength over time.

The multichannel spectrophotometer of the present invention tested over a period of time shows a high degree of stability, drift of less than $2 \times 10^{-4}$ AU/° C. or $2 \times 10^{-4}$ AU/hour after warm up, a noise level of $\pm 2 \times 10^{-5}$ AU in the range of 210–280 nm using a standard low volume flow cell in the sample cell with standard flow conditions, and a spectral range of 190–700 nm.

While preferred embodiments of the invention have been illustrated and described, the invention is not intended to be limited to the exact embodiment illustrated. The scope of the invention is intended to be determined by reference to the claims and their equivalents interpreted in light of the prior art.

We claim:

1. A pipeline sample and processing method for detecting a multiwavelength spectrum of the absorbance of radiation by a sample in a liquid solution within a sample cell using a dual beam system in which the first beam passes through the sample cell and the second beam passes through a reference cell, comprising the steps of:

dispersing the two beams of radiation by impinging the beams onto a grating to define a first and a second multiwavelength spectra;

directing the first wavelength spectra to a first linear array of photodetectors with different wavelength spectra being intercepted by different photodetectors;

directing the second multiwavelength spectra to a second linear array of photodetectors with different wavelength spectra being intercepted by different photodetectors;

separately and sequentially sampling and holding signals from the first array of photodetectors to form a sequence of sample signal voltages;

separately and sequentially sampling and holding signals from the second array of photodetectors to form a sequence of reference signal voltages wherein the sequence of reference signal voltages is synchronized with the sequence of sample signal voltages, such that there are corresponding sample signal voltages and reference signal voltages for the same spectral wavelength;

processing a corresponding sample signal voltage and reference signal voltage by discharging the reference signal voltage to decay exponentially to said corresponding sample signal voltage and determining the time interval of the decay, wherein the time interval is proportional to the logarithm of the ratio of the reference signal voltage to the sample signal voltage, and wherein the logarithm is proportional to the absorbance of the sample at the spectral wavelength associated with said corresponding signal voltages, wherein the step of processing, is repeated in sequence for subsequent corresponding sample signal and reference signal voltages such that pipelining of corresponding signals occurs for sampling, holding and processing.

2. A dual beam full spectrum multichannel spectrophotometer comprising:
   A. a single light source;
   B. an aperture defining a cone of light from the light source;
   C. a first pair of concave front surface mirrors reflecting and directing a pair of equivalent light beams, a reference beam and a sample beam, from the cone of light on to a pair of flat front surface mirrors which respectively redirect the beams away from the light source into a pair of optical cells, a reference cell and a sample cell, the first pair of concave front surfaced mirrors and the flat front surfaced mirrors being arranged such that the first pair of concave front surfaced mirrors focus the beam on the optical cells respectively and that the angles between the incident light beam and the reflected light beam at the first surfaced mirrors are less that 20°;
   D. a second pair of concave front surface mirrors for directing the reference beam and sample beam from the reference and sample cell respectively to a single flat grating for dispersing each of the beams into a spectrum, the second pair of concave front surface mirrors being arranged such that the second pair of front surfaced concave mirrors focus the beams respectively on a pair of photodiode arrays each with from about 30-70 elements and that the angles between the incident light beam and the reflected light beam at both the second pair of concave front surfaced mirrors and the grating are less than 20°; and
   E. the pair of photodiode arrays, a reference photodiode array and a sample photodiode array intercept each of the spectrums and convert the intensity of the light to reference electrical signal and sample electrical signal; and
   F. a data converter to convert the reference electrical signal and sample electrical signal from the pair of photodiode arrays into absorbance units.

3. A dual beam full spectrum multichannel spectrophotometer according to claim 2 further comprising a filter interposed between the source and the aperture to filter out second order effects.

4. A dual beam full spectrum multichannel spectrophotometer according to claim 2 wherein the angles between the incident light beam and the reflected light at the first pair of concave front surfaced mirrors are about 12.4° and at the flat front surfaced mirrors are about 11.5° and the angles between the incident light beam and the reflected light beam at both the second pair of concave front surfaced mirrors and the grating are about 15.8°.

5. A dual beam full spectrum multichannel spectrophotometer according to claim 3 wherein the angles between the incident light beam and the reflected light at the first pair of concave front surfaced mirrors are about 12.4° and at the flat front surfaced mirrors are about 11.5° and the angles between the incident light beam and the reflected light beam at both the second pair of concave front surfaced mirrors and the grating are about 15.8°.

6. A dual beam full spectrum, multichannel spectrophotometer according to claim 2 wherein the data converter comprises:
   (i) a means for selecting the electrical signals corresponding to a particular reference photodiode element and sample photodiode element;
   (ii) a means for converting each of the electrical signals to a voltage signal;
   (iii) a means for storing the reference signal and discharging the reference signal voltage to exponentially decay to the sample signal voltage level;
   (iv) a means for determining the time interval in which the reference signal voltage decays to the sample signal voltage, wherein the time interval is proportional to the logarithm of the ratio of the reference signal voltage to the sample signal voltage and wherein such logarithm is proportional to the absorbance of light by the sample; and
   (v) means for repeating steps (i) and (iv) for each pair of the reference electrical signal and sample electrical signal in each element of the photodiode arrays.

7. A dual beam full spectrum multichannel spectrophotometer according to claim 3 wherein the data converter comprises:
   (i) a means for selecting the electrical signals corresponding to a particular reference photodiode element and sample photodiode element;
   (ii) a means for converting each of the electrical signals to a voltage signal;
   (iii) a means for storing the reference signal and discharging the reference signal voltage to exponentially decay to the sample signal voltage level;
   (iv) a means for determining the time interval in which the reference signal voltage decays to the sample signal voltage, wherein the time interval is proportional to the logarithm of the ratio of the reference signal voltage to the sample signal voltage and wherein such logarithm is proportional to the absorbance of light by the sample; and (v) means for repeating steps (i) and (iv) for each pair of the reference electrical signal and sample electrical signal in each element of the photodiode arrays.

8. A dual beam full spectrum multi-channel spectrophotometer according to claim 4 wherein the data converter comprises:

(i) a means for selecting the electrical signals corresponding to a particular reference photodiode element and sample photodiode element;

(ii) a means for converting each of the electrical signals to a voltage signal;

(iii) a means for storing the reference signal and discharging the reference signal voltage to exponentially decay to the sample signal voltage level;

(iv) a means for determining the time interval in which the reference signal voltage decays to the sample signal voltage, wherein the time interval is proportional to the logarithm of the ratio of the reference signal voltage to the sample signal voltage and wherein such logarithm is proportional to the absorbance of light by the sample; and (v) means for repeating steps (i) and (iv) for each pair of the reference electrical signal and sample electrical signal in each element of the photodiode arrays.

9. A dual beam full spectrum multi-channel spectrophotometer according to claim 5 wherein the data converter comprises:

(i) a means for selecting the electrical signals corresponding to a particular reference photodiode element and sample photodiode element;

(ii) a means for converting each of the electrical signals to a voltage signal;

(iii) a means for storing the reference signal and discharging the reference signal voltage to exponentially decay to the sample signal voltage level;

(iv) a means for determining the time interval in which the reference signal voltage decays to the sample signal voltage, wherein the time interval is proportional to the logarithm of the ratio of the reference signal voltage to the sample signal voltage and wherein such logarithm is proportional to the absorbance of light by the sample; and (v) means for repeating steps (i) and (iv) for each pair of the reference electrical signal and sample electrical signal in each element of the photodiode arrays.

10. A dual beam full spectrum multichannel spectrophotometer according to claim 2, wherein there are 38 elements in each photodiode array.

11. A dual beam full spectrum multichannel spectrophotometer according to claim 3, wherein there are 38 elements in each photodiode array.

12. A dual beam full spectrum multichannel spectrophotometer according to claim 4, wherein there are 38 elements in each photodiode array.

13. A dual beam full spectrum multichannel spectrophotometer according to claim 5, wherein there are 38 elements in each photodiode array.

14. A dual beam multichannel spectrophotometer for detecting a multiwavelength spectrum of the absorbance of radiation by a sample in a liquid solution within a sample cell, comprising:

a source for generating two beams of radiation;

a means for dispersing the two beams of radiation comprising a grating, wherein the beams impinge onto said grating to define a first and a second multiwavelength spectra;

a first linear array of photodetectors for receiving said first multiwavelength spectra wherein different wavelength spectra are intercepted by different photodetectors;

a second linear array of photodetectors for receiving said second multiwavelength spectra wherein different wavelength spectra are intercepted by different photodetectors;

a means for separately and sequentially sampling and holding signals from the first array of photodetectors to form a sequence of sample signal voltages;

a means for separately and sequentially sampling and holding signals from the second array of photodetectors to form a sequence of reference signal voltages wherein the sequence of reference signal voltages is synchronized with the sequence of sample signal voltages, such that there are corresponding sample signal voltages and reference signal voltages for the same spectral wavelength;

a means for processing a corresponding sample signal voltage and reference signal voltage by discharging the reference signal voltage to decay exponentially to said corresponding sample signal voltage;

a means for determining the time interval of said decay, wherein the time interval is proportional to the logarithm of the ratio of the reference signal voltage to the sample signal voltage, and wherein the logarithm is proportional to the absorbance of the sample at the spectral wavelength associated with said corresponding signal voltages, a means for controlling the timing for both said means for separately and sequentially sampling and holding, said processing means and said determining means so as to pipeline subsequent corresponding sample signal and reference signal voltages for sampling, holding and processing.

* * * * *